US009764110B2

(12) United States Patent
Larson et al.

(10) Patent No.: US 9,764,110 B2
(45) Date of Patent: Sep. 19, 2017

(54) BINAURAL SLEEP INDUCING SYSTEM (71) Applicant: Mind Rocket, Inc., Colorado Springs, CO (US)

(72) Inventors: Michael C. Larson, Colorado Springs, CO (US); Jesse McClure, Colorado Springs, CO (US)

(73) Assignee: Mind Rocket, Inc., Colorado Springs, CO (US)

( * ) Notice: Subject to any disclaimer, the term of this patent is extended or adjusted under 35 U.S.C. 154(b) by 210 days.

(21) Appl. No.: 14/219,553

(22) Filed: Mar. 19, 2014

(65) Prior Publication Data

US 2014/0343354 A1 Nov. 20, 2014

Related U.S. Application Data (60) Provisional application No. 61/804,234, filed on Mar. 22, 2013.

(51) Int. Cl.
*A61M 21/02* (2006.01)
*A61B 5/00* (2006.01)
(Continued)

(52) U.S. Cl.
CPC ............. *A61M 21/02* (2013.01); *A61B 5/048* (2013.01); *A61B 5/0482* (2013.01); *A61B 5/486* (2013.01);
(Continued)

(58) Field of Classification Search
CPC ....... A61B 5/0476; A61B 5/11; A61B 5/4809; A61B 5/4812; A61B 5/04004–5/04009;
(Continued)

(56) References Cited

U.S. PATENT DOCUMENTS 5,036,858 A * 8/1991 Carter .................. A61B 5/0482
600/27
5,135,468 A 8/1992 Meissner
(Continued)

FOREIGN PATENT DOCUMENTS

EP 2537550 A1 6/2011
JP 2003-199831 12/2001
(Continued)

OTHER PUBLICATIONS

Teplan, M. "Fundamentals of EEG Measurement." Measurement Science Review 2.2 (2002): 1-11.*
(Continued)

*Primary Examiner* — Christine H Matthews
*Assistant Examiner* — Kaylee Wilson
(74) *Attorney, Agent, or Firm* — Martensen IP (57) ABSTRACT By using an iterative loop of data collection, binaural tone generation/presentation, and analysis binaural tones can be introduced to induce an existing brain state to change from one associated with being awake to a state associated with being asleep. The current state of an individual's brain is determined by measuring movement and electrical activity. Using this data a binaural tone can be generated to induce the brain state to change. As the state of the brain is continually monitored the applied binaural tone is modified and applied until the desired sleep state is obtained.

32 Claims, 4 Drawing Sheets

(51) Int. Cl.
*A61B 5/048* (2006.01)
*A61B 5/0482* (2006.01)
A61B 5/0476 (2006.01)
A61B 5/11 (2006.01)
A61B 5/04 (2006.01)
A61M 21/00 (2006.01)

(52) U.S. Cl.
CPC .......... *A61B 5/4809* (2013.01); *A61B 5/4812* (2013.01); *A61B 5/04001* (2013.01); *A61B 5/04008* (2013.01); *A61B 5/0476* (2013.01); *A61B 5/11* (2013.01); *A61B 5/7282* (2013.01); *A61M 2021/0027* (2013.01); *A61M 2230/10* (2013.01); *A61M 2230/63* (2013.01)

(58) Field of Classification Search
CPC ...... A61B 5/04845; A61M 2021/0027; A61M 2230/10; A61M 2230/63; A61M 21/00–21/02
See application file for complete search history.

(56) References Cited

U.S. PATENT DOCUMENTS

| | | | |
|---|---|---|---|
| 5,213,562 A | 5/1993 | Monroe | |
| 6,488,617 B1 * | 12/2002 | Katz | A61B 5/0482 600/26 |
| 7,041,049 B1 * | 5/2006 | Raniere | A61M 21/02 128/905 |
| 2007/0249952 A1 * | 10/2007 | Rubin | A61B 5/0476 600/544 |
| 2008/0071136 A1 * | 3/2008 | Oohashi | A61M 21/02 600/27 |
| 2009/0192556 A1 | 7/2009 | Wu | |
| 2010/0010289 A1 | 1/2010 | Clare | |
| 2010/0087701 A1 * | 4/2010 | Berka | A61M 21/02 600/27 |
| 2011/0009921 A1 | 1/2011 | Tass | |
| 2013/0303837 A1 * | 11/2013 | Berka | A61M 21/02 600/28 |

FOREIGN PATENT DOCUMENTS

WO  2013028960 A1  2/2013
WO  WO 2013028960 A1 *  2/2013  ........... A61B 5/4806

OTHER PUBLICATIONS

Extended European Search Report; Oct. 14, 2016; Application No. 14770415.9.

* cited by examiner

BINAURAL SLEEP INDUCING SYSTEM

RELATED APPLICATION

The present application relates to and claims the benefit of priority to U.S. Provisional Patent Application No. 61/804,234 filed 22 Mar. 2013 which is hereby incorporated by reference in its entirety for all purposes as if fully set forth herein.

BACKGROUND OF THE INVENTION

1. Field of the Invention

Embodiments of the present invention relate, in general, to inducing sleep and more particularly to inducing an individual to a sleep state using binaural acoustic tones.

2. Relevant Background

Over 40 million people in the United States alone suffer from sleep problems. And almost everyone occasionally suffers from short-term insomnia. Sleep disorders and insomnia can result from stress, jet lag, diet, or many other factors. Insomnia almost always affects job performance and wellbeing the next day and its occurrence tends to increase with age. Some 40 percent of women and 30 percent of men are impacted by sleep disorders.

Sleeping pills are the first line of defense for short-term insomnia. Most sleeping pills stop working after several weeks of nightly use, however, and long-term use can actually interfere with good sleep. Mild insomnia often can be prevented or cured by practicing good sleep habits such as relaxing before trying to go to sleep, taking a hot bath, reading a book, winding down, etc. For more serious cases of insomnia, researchers are experimenting with light and sound therapy to alter circadian cycles.

Any amount of sleep deprivation will diminish mental performance. Indeed one complete night of sleep deprivation can be as impairing in simulated driving tests as a legally intoxicating blood-alcohol level. Moreover, people who regularly do not get enough sleep can become less sensitive to insulin and other medications.

Just as the lack of sleep can diminish a person's wellbeing and pose serious health risks, there are well known benefits to gaining adequate sleep. For example, it is well known that growth hormones in children are secreted during sleep, and chemicals important to the immune system are secreted during sleep. Studies have shown that a person can become more prone to disease if they do not receive enough sleep.

No one really knows why animals (humans) sleep. One theory is that sleep gives the body a chance to repair muscles and other tissues, replace aging or dead cells, etc. Sleep, it is believed, gives the brain a chance to organize and archive memories. Dreams are thought by some to be part of this process. Sleep also lowers our energy consumption, so we need three meals a day rather than four or five. While through the use of technology we have, as a species, become more and more adept to working in the night, humans are fundamentally diurnal. One theory is that our body is simply programmed to preserve energy until the sun comes up.

Until the 1950s, most people thought of sleep as a passive, dormant part of one's daily life. Research has determined that a human's brain is very active during sleep. Nerve-signaling chemicals called neurotransmitters control whether one is asleep or awake by acting on different groups of nerve cells, or neurons, in the brain. Neurons in the brainstem, which connects the brain with the spinal cord, produce neurotransmitters such as serotonin and norepinephrine that keep some parts of the brain active during waking moments. Other neurons at the base of the brain begin signaling during the transition from being awake to being asleep. These neurons appear to "switch off" the signals that keep us awake. Research also suggests that a chemical called adenosine builds up in our blood while we are awake and causes drowsiness. This chemical gradually breaks down while we sleep.

While asleep, an individual usually passes through five phases of sleep: stages 1, 2, 3, 4, and REM (rapid eye movement) sleep. These stages progress in a cycle from stage 1 to REM sleep, then the cycle starts over again with stage 1. We spend almost 50 percent of our total sleep time in stage 2 sleep, about 20 percent in REM sleep, and the remaining 30 percent in the other stages. Infants, by contrast, spend about half of their sleep time in REM sleep.

During stage 1, which is light sleep and associated with theta waves, an individual drifts in and out of sleep and can be awakened easily. During this stage eyes move very slowly and muscle activity slows. People awakened from stage 1 sleep often remember fragmented visual images. Many also experience sudden muscle contractions called hypnic myoclonia, often preceded by a sensation of starting to fall. When a person enters stage 2 sleep, eye movements stop and brain waves (fluctuations of electrical activity that can be measured by electrodes) become slower, with occasional bursts of rapid waves called sleep spindles. In stage 3, extremely slow brain waves called delta waves begin to appear, interspersed with smaller, faster theta waves. By stage 4, the brain produces delta waves almost exclusively and it is very difficult to wake someone during stages 3 and 4, which together are commonly referred to as deep sleep. There is no eye movement or muscle activity during this stage of sleep. People awakened during deep sleep do not adjust immediately and often feel groggy and disoriented for several minutes after they wake up. It is in this stage that children experience bedwetting, night terrors, or can sleep walk.

When a person switches into REM sleep, their breathing becomes more rapid, irregular, and shallow, their eyes jerk rapidly in various directions, their limb muscles become temporarily paralyzed, the heart rate increases and blood pressure rises. And when people awaken during REM sleep, they often describe bizarre and illogical tales—dreams.

Each of these stages or states of consciousness is also associated with specific amount of brain activity. By attaching an electroencephalograph to a person's head you can record the person's brainwave activity. An awake and relaxed person generates alpha waves, which are consistent oscillations at about 10 cycles per second. An alert person generates beta waves, which are about twice as fast.

Beta waves typically range between 12 and 40 hertz (hz). This is generally the mental state most people are in during the day and most of their waking lives. Usually, this state in itself is uneventful but it is important. Many people lack sufficient beta activity, which can cause mental or emotional disorders such as depression and insomnia. And low beta wave production (a sub-range of beta at 12-15 hz) may be related to insomnia and according to one theory stimulating beta activity can improve emotional stability, energy levels, attentiveness and concentration, as well as the ability to fall asleep. Simply put, an individual that is mentally exhausted may find it easier to fall asleep.

Conversely alpha waves predominantly originate from the occipital lobe during wakeful relaxation with closed eyes. Alpha waves are reduced with open eyes, drowsiness and sleep. Historically, they were thought to represent the activity of the visual cortex in an idle state. More recent papers have argued that they inhibit areas of the cortex not in use, or alternatively that they play an active role in network coordination and communication. Occipital alpha waves during periods of eyes closed are the strongest EEG brain signals.

Alpha waves, 8-13 hz, are associated with being awake but relaxed and not processing much information. When a person gets up in the morning, and just before sleep, they are naturally in this state. The brain automatically starts producing more alpha waves when the eyes are closed.

Theta waves, which are characterized from 3-8 hz appears to be a transitional state of light sleep or extreme relaxation. Brain activity producing delta waves 0.2-3 hz is accepted by most studies as being asleep. Delta waves are the slowest, but highest amplitude brainwaves. Delta waves begin to appear in stage 3 sleep, but by stage 4 nearly all spectral activity is dominated by delta waves. Stage 3 sleep is defined as having less than 50% delta wave activity, while stage 4 sleep has more than 50% delta wave activity. Delta waves occur in all mammals, and potentially in all animals as well.

While scientists can validate through devices such as an EEG that when an individual is relaxed or asleep they produce alpha or delta waves respectively assisting one to arrive at that state remains a challenge. Sleep remains for many an illusive goal keeping the treatment of insomnia a major focus of many research laboratories and commercial markets. These and other challenges with respect to the treatment of insomnia and other sleep disorders are address by one or more embodiments of the present invention.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

SUMMARY OF THE INVENTION

Using binaural tones, the system of the present invention induces the brain to slow down and transition from a state of wakefulness to that of rest. A system for inducing brain state changes includes an accelerometer to detect motion and a sensor to detect electrical brain activity determines the current state of an individual's brain. A microcontroller is included that analyzes the data to determine an intermediate brain state interposed between the current brain state and a goal state. Using a binaural generator, binaural tones based on the intermediate brain state are presented to the individual to influence the brain to change from the current state to that consistent with the intermediate state. The state of the brain is continually monitored and the determination of the intermediate state and associated application of the binaural tones are modified to provide a continuous application of modified binaural tones until the desired goal state is achieved.

According to another embodiment of the present invention, a system for inducing sleep includes a sensor operable to detect brain activity, an accelerometer operable to detect changes in motion, a binaural tone generator, a processor and a plurality of software code. Portions of the software code are configured to determine a current brain state based on detected brain activity and detected changes in motion and to create a binaural tone from the binaural tone generator based on current brain state, a target brain state and an intermediate target brain state.

A method embodiment for inducing sleep according to the present invention using binaural tones includes collecting brain state data and analyzing the collected data to determine an activity state. The process continues by comparing the activity state to a goal state and responsive to the activity state differing from the goal state, determining a suggestive binaural tone frequency and an intermediate goal state. Thereafter the process applies the suggestive binaural tone to adjust the activity state to the intermediate goal state while monitoring the activity brain state to determine whether the suggestive binaural tone influences the activity brain state toward the intermediate goal state. Lastly, responsive to the suggestive binaural tone changing the activity brain state toward the intermediate goal state, the method adjusts the intermediate goal state and the suggestive binaural tone.

The features and advantages described in this disclosure and in the following detailed description are not all-inclusive. Many additional features and advantages will be apparent to one of ordinary skill in the relevant art in view of the drawings, specification, and claims hereof. Moreover, it should be noted that the language used in the specification has been principally selected for readability and instructional purposes and may not have been selected to delineate or circumscribe the inventive subject matter; reference to the claims is necessary to determine such inventive subject matter.

BRIEF DESCRIPTION OF THE DRAWINGS

The aforementioned and other features and objects of the present invention and the manner of attaining them will become more apparent, and the invention itself will be best understood, by reference to the following description of one or more embodiments taken in conjunction with the accompanying drawings, wherein.

The Figures depict embodiments of the present invention for purposes of illustration only. One skilled in the art will readily recognize from the following discussion that alternative embodiments of the structures and methods illustrated herein may be employed without departing from the principles of the invention described herein.

DESCRIPTION OF THE INVENTION

For many a good night's sleep is an illusive goal. Insomnia affects millions of people worldwide. In some respects the mechanisms involved with sleep still elude us. While science has been able to reach some broad conclusions with respect to sleep it remains, at an individual level, a very difficult phase to predict. Why, for example, can one individual seem to require very little sleep while another requires 10 or more hours to feel rested? And why do some individuals quickly and soundly fall asleep while others toss and turn all night? Certainly may theories have been forwarded as to the causes for sleep disorders and through such investigation has developed a better understanding of how the brain operates as it transitions from an awake to resting state. The present invention capitalizes on this understanding and presents a system to induce changes in brain activity using binaural tones. Accordingly, various embodiments of the present invention use binaural tones to drive, and in some embodiments maintain, brain activity to a sleep state. By identifying and monitoring an individual's brain activity state a correct binaural tone can be applied to induce the brain activity to slow from one of being awake and active to one that is associated with being drowsy and eventually asleep. Moreover the embodiments of the present invention presented herein can facilitate an individual to achieve a state of deep restful sleep rather than one of light, restless slumber.

Embodiments of the present invention are hereafter described in detail referencing the accompanying Figures. Although the invention has been described and illustrated with a certain degree of particularity, it is understood that the present disclosure has been made only by way of example and that those skilled in the art can resort to numerous changes in the combination and arrangement of parts without departing from the spirit and scope of the invention.

The following description and drawings are provided to assist in a comprehensive understanding of exemplary embodiments of the present invention as defined by the claims and their equivalents. It includes various specific details to assist in that understanding but these are to be regarded as merely exemplary. Accordingly, those of ordinary skill in the art will recognize that various changes and modifications of the embodiments described herein can be made without departing from the scope and spirit of the invention. Also, descriptions of well-known functions and constructions are omitted for clarity and conciseness.

The terms and words used in the following description and claims are not limited to the bibliographical meanings, but are merely used by the inventor to enable a clear and consistent understanding of the invention. Accordingly, it should be apparent to those skilled in the art that the following description of exemplary embodiments of the present invention are provided for illustration purpose only and not for the purpose of limiting the invention as defined by the appended claims and their equivalents.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Like numbers refer to like elements throughout. In the figures, the sizes of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. Thus, for example, reference to "a component surface" includes reference to one or more of such surfaces.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be also understood that when an element is referred to as being "on," "attached" to, "connected" to, "coupled" with, "contacting", "mounted" etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of a device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

Included in the description are flowcharts depicting examples of the methodology that may be used to induce sleep using binaural tones. In the following description, it will be understood that each block of the flowchart illustrations, and combinations of blocks in the flowchart illustrations, can be implemented by computer program instructions. These computer program instructions may be loaded onto a computer or other programmable apparatus to produce a machine such that the instructions execute on the computer or other programmable apparatus to create a means for implementing the functions specified in the flowchart block or blocks. These computer program instructions or code may also be stored in a computer-readable memory that can direct a computer or other programmable apparatus to function in a particular manner such that the instructions stored in the computer-readable memory produce an article of manufacture including instruction means that implement the function specified in the flowchart block or blocks. The computer program instructions may also be loaded onto a computer or other programmable apparatus to cause a series of operational steps to be performed in the computer or on the other programmable apparatus to produce a computer implemented process such that the instructions that execute on the computer or other programmable apparatus provide steps for implementing the functions specified in the flowchart block or blocks.

Accordingly, blocks of the flowchart illustrations support combinations of means for performing the specified functions and combinations of steps for performing the specified functions. It will also be understood that each block of the flowchart illustrations, and combinations of blocks in the flowchart illustrations, can be implemented by special purpose hardware-based computer systems that perform the specified functions or steps, or combinations of special purpose hardware and computer instructions.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve the manipulation of information elements. Typically, but not necessarily, such elements may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," "words", or the like. These specific words, however, are merely convenient labels and are to be associated with appropriate information elements.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

Upon reading this disclosure, those of skill in the art will appreciate still additional alternative structural and functional designs for a system and a process for inducing sleep using binaural tones through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

Figure 1:
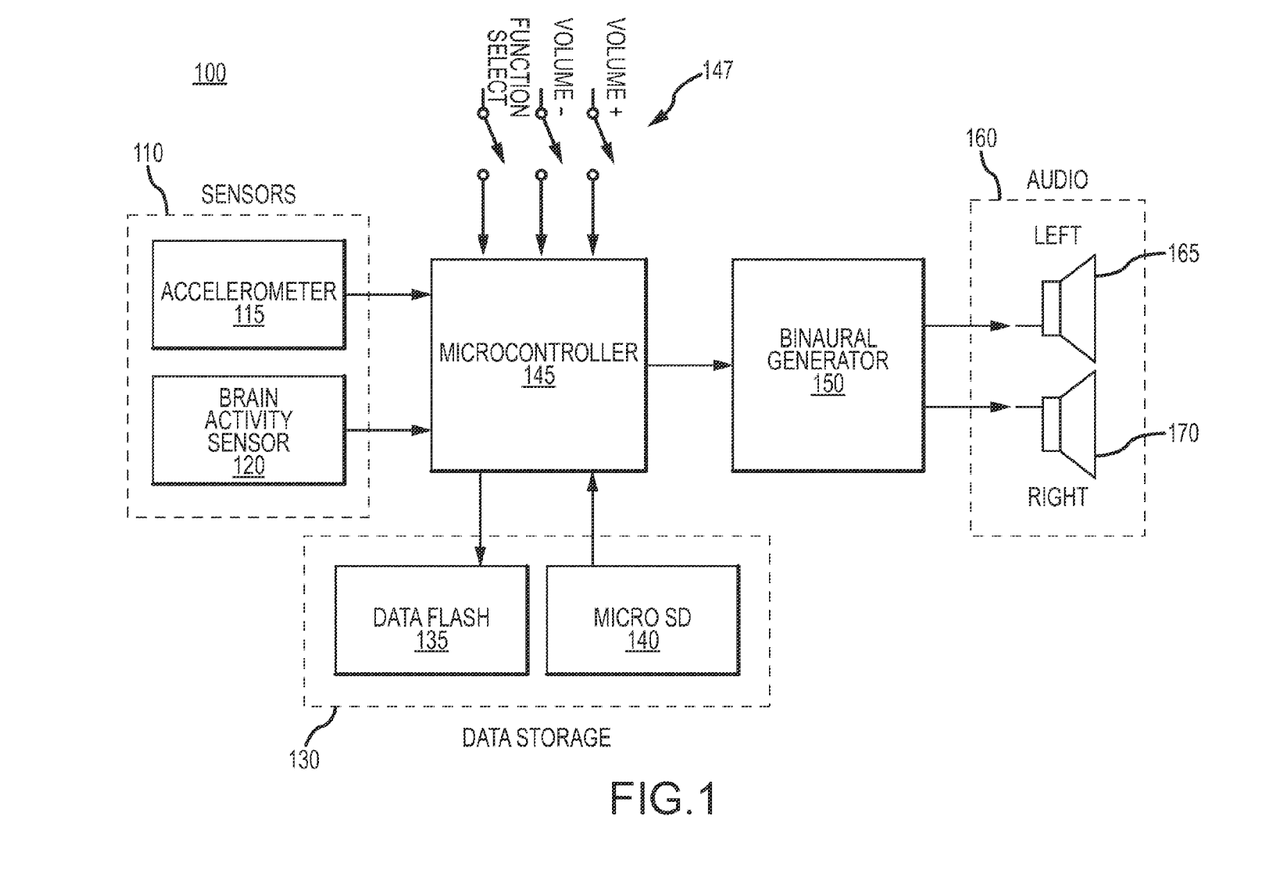
FIG. 1 is a high-level block diagram of a system for inducing sleep using binaural tones.

FIG. 1 presents a high-level block diagram of a system for inducing sleep using binaural tones according to one embodiment of the present invention. The sleep inducing system 100 of the present invention includes a microcontroller 145 coupled to a plurality of sensors 110 and a binaural tone generator 150. As can be seen in FIG. 1 the binaural tone generator 150 is further coupled to an audio output device 160 that can, in one embodiment, include a left speaker 165 and a right speaker 170. In addition, the microcontroller 145 is coupled to a non-volatile memory device 130 for the storage of data and certain instructions that are used by processors within the microcontroller 145.

A binaural tone is a physical phenomenon that when two different frequencies are presented separately, one to each ear, the human brain detects the phase variation between the frequencies and tries to reconcile that difference. For example, if a frequency of 100 Hz is presented to your left ear, and a frequency of 105 Hz is presented to your right ear, your brain "hears" a third frequency pulsing at 5 Hz, the exact difference between the two frequencies. This perceived frequency is known as a binaural tone or beat. The tone does not really exist. That is, there is no 5 Hz tone. It is that the brain perceives the two different tones as a single 5 Hz tone. In some cases a binaural beat will cause the brain to begin resonating in tune with that beat. By creating the correct binaural tone an individual's brain can begin to resonate with the tone and follow the beat. The present invention identifies an individual's current brain activity state and thereafter creates a binaural tone to which the brain can resonate. With a brain resonance established the tone can be adjusted thus influencing an individuals brain state.

The human brain typically operates from between 0.5 and 30 Hz. In its most active state the brain is pulsing away at a state somewhere above 14 Hz. Higher mental activity occurs around 40 Hz while typical day-to-day "awake" activity is somewhere around 20 Hz. This "awake" state is associated with beta waves. Alpha waves, which are characterized as being between 8 and 13 Hz, are associated with a relaxed or drowsy state. Meditation and deep relaxation strives to achieve an alpha wave state.

Brain activity below 8 Hz is considered asleep. Sleep, nonetheless, has several different stages. Stage 1, 4-7 Hz, is characterized as theta waves and is a very light sleep condition in which activity slows and occasional muscle twitching is observed. Rapid eye movement does not occur. Within this stage body temperature drops, the heart rate slows and the body appears to enter a recovery or repair cycle.

Below 4 Hz the human brain enters a very deep stage of sleep know to produce delta waves. This is where dreaming and rapid eye movement occurs. To feel rested an individual must achieve and maintain for a period of time this stage of sleep. The present invention induces the brain in a following response to produce delta waves so that the individual can enter this very deep stage of sleep.

According to one embodiment of the present invention, binaural tones are created that influence brain activity. Moreover, the present invention measures brain activity so that the binaural tone presented is suitable for the individual's current brain state.

Turning attention back to FIG. 1, the sleep inducing system 100 of the present invention includes a plurality of sensors 110 that collect data representative of brain state. These sensors can include, in one embodiment of the present invention, accelerometers 115 to detect and measure movement, and brain activity sensors 120 to collect data with respect to electrical impulses generated by the brain.

Actigraphy is a non-invasive method of monitoring human rest/activity cycles Actigraphy testing consists of a small portable device (actigraph) that senses physical motion and stores the resulting information such in the data storage device 130 of the present invention. Actigraphy testing is based on the assumption that movement is reduced during sleep compared with wakefulness and that activity level can be used as a diagnostic indicator for sleep disorders.

Movement alone however is not a reliable measure of ones brain activity. Therefore, and according to one embodiment of the present invention, a second sensor 120 is used to capture brain activity.

The brain's electrical charge is maintained by billions of neurons. These neurons are electrically charged and are constantly exchanging ions among themselves. Devices such as an electroencephalograph (EEG) can measure the summation of millions of these neurons that have similar spatial orientation. This activity oscillates in a wave formation that gives rise to the various characterizations of beta, alpha and delta brain states.

Another means by which to measure brain activity is by using magnetic fields created by the brain's electrical signals. Such a technique is called magnetoencphalography (MEG). Unlike an EEG, an MEG can observe and measure brain activity deep within the brain.

The present invention collects data with respect to an individuals current brain state. While devices such as EEGs and MEGs can provide an accurate assessment of the state or one's brain, the data can be difficult to interpret. Accordingly the present invention collects and synthesizes data from a plurality of sources to determine the individual's current brain activity state.

The system of the present invention further includes algorithms useful in the analysis of collected data and the development of binaural tones that can effectively influence brain activity. According to one embodiment of the present invention one or more algorithms embodied as software are stored in nonvolatile storage 130, in media such as data flash 135 or a microSD card 140. These instructions are operable to synthesize information regarding the motion of an individual gained via an accelerometer 115 or similar sensor with that of brain activity measured by a brain activity sensor 120 such as an EEG.

In one embodiment of the present invention a sleeping hat or similar device is constructed to include the system components shown in FIG. 1. Sensors 110 are positioned within the device to collect and measure brain activity and motion simultaneously. The tools used for the collection of electrical brain activity vary widely. Such devices utilize a plethora of electrodes positioned over much of an individual's skull. While such configurations facilitate an accurate and complete collection of electrical brain activity they are not very conducive to the wearer achieving a restful state of sleep.

According to one embodiment of the present invention, the system for inducing sleep includes a singular electrical sensor positioned upon the individual's forehead. The sensor is configured as a surface contact electrode ideally positioned flat against the user's skin and held in place by an elastic band or similar device to apply minimal, yet effective compression. Another electrode, serving as a ground, is in contract with the individual's skin near one or both ears. Similarly that electrode is held in place using an elastic band or clip. As one of reasonable skill in the relevant art can appreciate the simplified configuration of electrodes of the present invention cannot replace the robust electrode configurations found in a full EEG. Thus and according to one embodiment of the present invention, brain activity data collected by this sensor 120 is combined, synthesized, with data regarding the individual's motion. Combined, the present invention develops an accurate assessment of the current brain state that can thereafter enable the system to determine an appropriate and influential binaural tone.

As discussed above, the present invention collects data to determine a current brain activity state. Using this information and instructions embodied as software, the microcontroller 145 identifies an intermediate brain state interposed between the current brain activity state and a target or goal brain state. If for example an individual's goal in using the system of the present invention is to arrive at a state of deep sleep associated with delta waves of 0.5-3 Hz, and the individual's current brain state is at 15 Hz which is associated with being awake, the present invention will identify an intermediate target interposed between the target 0.5-3 Hz and the current state of 15 Hz. For example the system may identify an intermediate state of 12 Hz.

Using this identified intermediate state the microcontroller 145 provides instructions to the binaural tone generator to create binaural tones in the left 165 and right 170 audio devices 160 of the present invention to create a binaural beat or tone consistent with the intermediate state. Note that while the goal of the device and system is to arrive at a state of restful sleep associated with delta waves at 0.5-3 Hz, the present invention does not apply binaural tones consistent with the target or goal but rather an obtainable and influential intermediate state.

By doing so the present invention influences the brain state in controlled and almost imperceptible steps. The system of the present invention continually monitors and adjusts the determined current brain state of the individual so that in turn the intermediate goal and binaural tones presented to the user can be modified. The process of the present invention is thus iterative in that it continually assesses the ability of the binaural tones to influence an individual's brain state.

As an individual's current brain state approaches the target brain state the intermediate and target state become concurrent. And upon achieving the target brain state the presentation of binaural tones ceases so as to enable the individual to enter and maintain a restful sleep cycle naturally. Data collection continues so that should it appear that the user is not remaining in the targeted zone, the system can reinitiate the presentation of binaural tones to place the user once again into the targeted zone.

The present invention also recognizes that it may be unable to influence an individual's brain activity. In a scenario in which, despite repeated attempts, the system cannot influence the brain activity to within the targeted zone, the system will, after a predetermined period of time, cease to operate.

Figure 2:
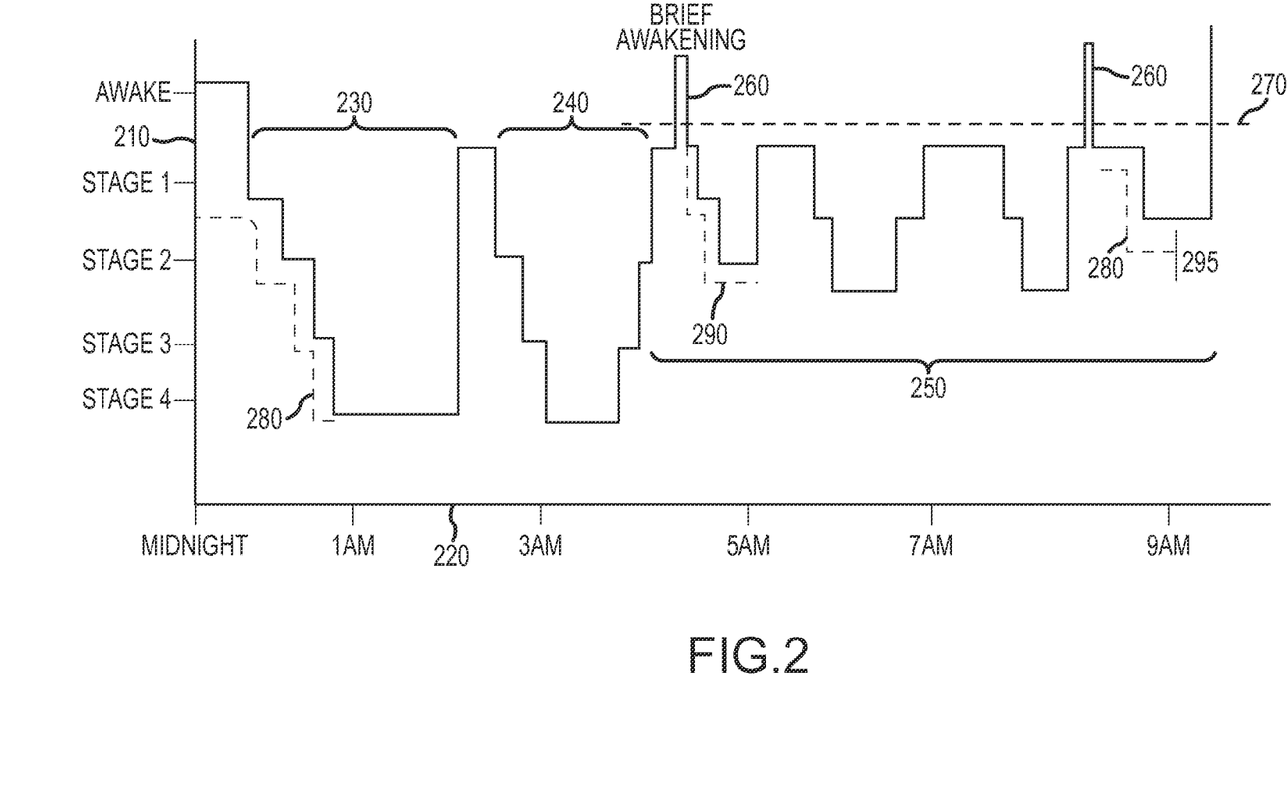
FIG. 2 is a graphical depiction of a typical sleep cycle including the moderated applications of binaural tones according to the present invention.

As one of reasonable skill in the relevant art will appreciate, an individual's sleep pattern varies throughout the night. One does not simply enter into and remain in state of delta waves throughout the entire night's sleep. FIG. 2 shows a typical sleep pattern. Each individual's sleep pattern is unique. Moreover each individual's pattern varies from night to night. A typical sleep pattern includes two or three periods of deep sleep followed by several additional periods of what is often referred to as light, stage 1 or 2, sleep.

FIG. 2 shows a histogram of a typical sleep pattern influenced by a sleep inducing system according to one embodiment of the present invention. As shown the graph shows several sleep cycles across a period of time represented by the horizontal axis 220 in which each cycle includes varying stages of sleep, shown on the vertical axis 210. The graph, at a high level, illustrates that individuals typically experience one or two cycles of deep sleep 230 early in the night, followed by several period of light sleep 250 until they awake in the morning. The graph also shows that during the periods of light sleep 250 individuals often experience brief awakenings 260.

According to one embodiment of the present invention, data collected by the system can be used to determine the brain state of the individual so as to properly provide binaural tones. FIG. 2 presents a graphical representation of the application of binaural tones 280 as associated with an individual's determined brain state. The dotted line 280 represents a leading application of binaural tones to entice the brain activity to achieve a goal state of stage 4 sleep. The system of the present invention identifies that the individual is awake as they lie down for sleep near midnight and produces a binaural tone consistent with stage 1 sleep even though the targeted sleep state is stage 4 sleep.

As the system monitors the brain state of the individual it recognizes that the individual has fallen asleep and achieved stage 1 sleep. Shortly thereafter the system adjusts the binaural tone so as to be consistent with stage 2 sleep. Again, the system monitors the brain's state and upon determining stage 2 sleep has been obtained the system once again modifies the binaural tone presentation. This iterative system continues until the individual reaches the targeted stage 4 sleep. At that time the binaural tone generator ceases to illicit the tones and the individual can transition in a normal sleep pattern. The above example of frequency modifications illustrates one embodiment of a decreasing frequency progression of binaural tones to induce sleep. The process is, in one embodiment, based on an iterative determination of current brain activity using collected brain activity data.

As sleep continues the system continues to monitor the individual's brain state. According to one embodiment of the present system, a predetermined brain state threshold 270 is established that, during the period of rest, should the individual's brain state exceed the system reinitiate binaural tones. In the sleep pattern shown in FIG. 2, a predetermined threshold 270 slightly above stage 1 sleep has been set to identify when the individual is in danger of prematurely awakening. According to one embodiment of the present invention, once the individual reaches the desired goal state, the system monitors brain activity to determine whether there is an additional need for the application of binaural tones.

Consider the instance wherein, after the individual has achieved two periods of deep stage 4 sleep, the individual appears to have a brief awakening 260. Sensors within the system may have detected movement and/or brain activity consistent with being awake rather than being asleep as expected. In this example, assume that a predetermine sleep period of 9 hours has been set 295 by the user meaning that upon initiation of the system the user expects (hopes) to sleep for 9 hours. Data indicating an awakening brain state 4 hours into the sleep period triggers a re-initiation of binaural tones.

According to one embodiment of the present invention, the microcontroller once again issues instructions to the binaural tone generator to provide binaural tones at a frequency slightly below the awakened state so as to induce stage 1 sleep. In one embodiment the binaural tones are set 1-3 hz below the current state. The system again steps the individual down into stage 2 or even stage 3 sleep. Typically an individual achieves one or two stages of deep sleep early in the night followed by several stages of lighter sleep. It would therefore be inappropriate for the system to retain the goal of stage 4 sleep at a point in the individual's sleep cycle in which a lighter stage 2 or three is more likely. According to one embodiment of the present invention, the system modifies the goal brain state so as to be consistent with a typical sleep cycle. As one of reasonable skill in the relevant art can appreciate, differences in sleep cycles will necessitate differing thresholds for re-initiation of binaural tones and for adjustments of the goal state. The present invention provides the means by which to collect historical data and modify the goal state and re-initiation threshold based on past sleep patterns.

Just as the present invention can induce an individual to sleep, the binaural tones can also induce an individual to awake. Moreover, if the awakening occurs during a period of light, stage 1, sleep individuals are likely to arise feeling rested and ready to get out of bed. Alternatively, awakening while in a deeper stage 2, or stage 3, sleep state results in feeling tired with a strong desire to stay in bed. One embodiment of the present invention includes a termination or wake time. In its simplest of modes the termination time 295 is a time limit upon the expiration of which binaural tones are no longer applied. In such an instance the individual will be thereafter allowed to wake up. In another embodiment of the present invention, reaching the termination time initiates binaural tones of a higher frequency. Just as binaural tones of a frequency lower than that of the current brain state influences the brain to slow down and enter a deeper state of sleep, providing binaural tones of a higher frequency can influence the brain to speed up and transition from a sleeping state to that of being awake. In such an instance the termination time limit can examine the current brain state and begin to slowly increase brain activity until the individual naturally wakes.

Figure 3:
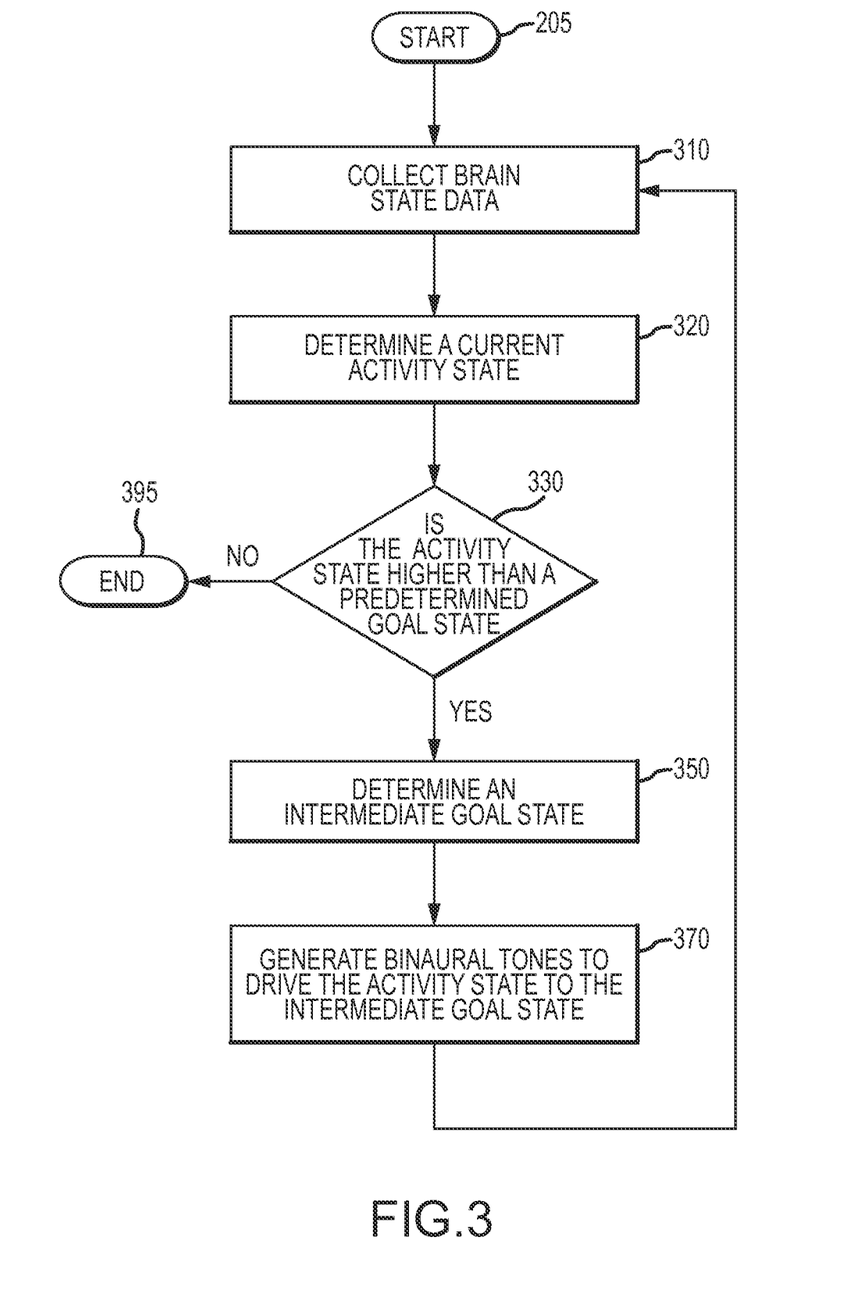
FIG. 3 is a high-level flowchart of a method for inducing sleep according to the present invention using binaural tones.

A high-level flowchart of a method for inducing sleep according to the present invention using binaural tones is presented in FIG. 3. The process begins 305 with the collection of brain state data 310. This data may be in the form of electrically observed brain waves or information regarding movement of the individual as they attempt to fall asleep. The information is collected and analyzed to determine a current activity brain state 320 of the individual.

Processors within the device execute instructions that compare 330 the determined current brain state to that of a predetermined goal state. If the current brain state is below that of the targeted or goal brain state the process ends 295. If however it is determined by comparison that the current brain state is higher than the goal state an algorithmic process is conducted whereby an intermediate goal state is determined 350.

This intermediate goal state is interposed between the current activity state of the brain and the desired state. The intermediate state is a step that can be obtained by the application and influence of binaural tones.

Accordingly binaural tones are generated 370 consistent with the intermediate goal state so as to drive brain activity lower and ultimately toward the goal. During this time the collection 310 of data and determination 320 of the current brain state continues. The process therefore adjusts the establishment of the intermediate step and binaural tone generation to as to drive (influence) the brain activity to achieve the desired goal.

Figure 4:
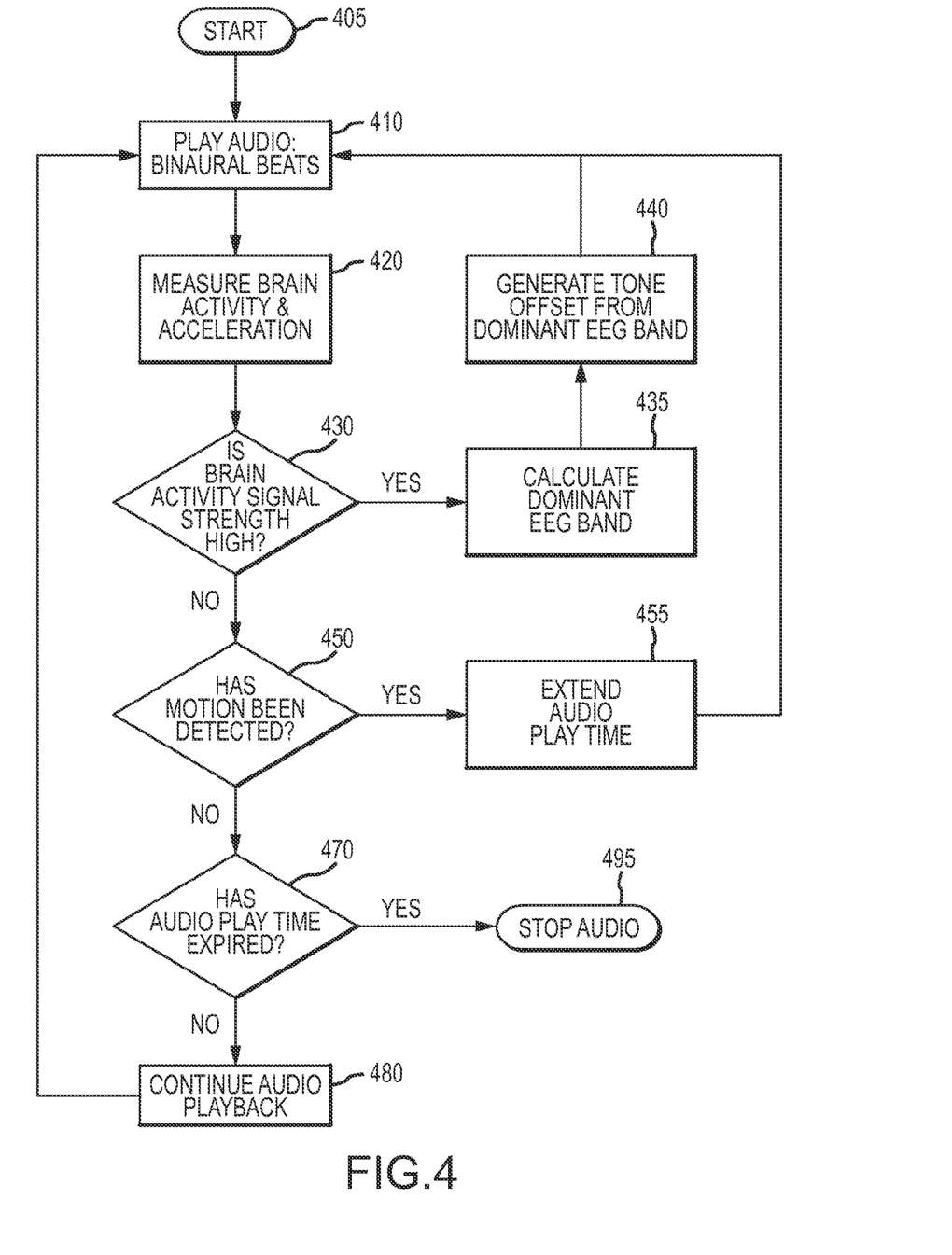
FIG. 4 presents a more detailed flowchart of a process to induce sleeping using binaural tones according to one embodiment of the present invention.

FIG. 4 presents a more detailed flowchart of a process to induce sleeping using binaural tones according to one embodiment of the present invention. The process shown in FIG. 4 begins 405 with user inputting data with respect to the desired sleep stage goal and duration of the sleeping event. In this embodiment of the present invention, the binaural tone generator plays binaural tones 410 as the sensors measure the activity state of the brain.

Measures are made of brain activity based on acceleration 420 or motion and electrical brain activity 430. With this information in hand a dominant electrical band of brain activity is identified 435. Based on this dominant band, a binaural tone is generated 440 that is slightly offset from that band so as to influence the brain to follow the binaural tone. The tone is played 410 and again data is collected 420, 430.

In situations in which electrical brain activity cannot reliably be gained and motion indicators 450 determine that the individual is still awake, the binaural tone generator can continue to generate binaural tones to influence the state of the brain.

In this embodiment the process described above continues iteratively until a predetermined time limit for audio play has expired 470. Upon expiration the process ends 495. If time has not expired, the audio playback continues 480, 410(?) and data is once again collected 420, 430 and analyzed 435.

The present invention uses an iterative loop of data collection, binaural tone generation/presentation, and analysis to induce an existing brain state to change from one associated with being awake to a state associated with being asleep. The system and associated methodology of the present invention determines the current state of an individual's brain by measuring movement and electrical activity. Synthesizing these measurements together, gaps in data from one type of sensor can be overcome so as to provide a reliable yet cost effective means by which to estimate the individual's stage of sleep.

Based on the current brain state and an established goal state, the system identifies an obtainable intermediate goal. This intermediate goal is slightly lower in frequency than the current brain state yet likely significantly above the ultimate goal of delta waves. Binaural tones are generated consistent with this intermediate goal and offset from the exiting current brain state. Once applied to earphones by the binaural generator, the tones in each headphone develop a binaural resonance within the brain. This binaural resonance induces the brain to match the beat and thus slow brain activity.

The process continues until the brain adjusts the binaural tones to the desired or goal state of delta brain waves. Upon reaching this state of deep sleep, the system terminates tone generation.

The present invention uses an iterative feedback system to enable a user to gradually lower their brain state to one or relaxation and ultimately sleep.

One familiar with the art of this invention will realize that the invention may be embodied in other specific forms without departing from the spirit or essential characteristics thereof. Likewise, the particular naming and division of the modules, managers, functions, systems, engines, layers, features, attributes, methodologies, and other aspects are not mandatory or significant, and the mechanisms that implement the invention or its features may have different names, divisions, and/or formats. Furthermore, as will be apparent to one of ordinary skill in the relevant art, the modules, managers, functions, systems, engines, layers, features, attributes, methodologies, and other aspects of the invention can be implemented as software, hardware, firmware, or any combination of the three. Of course, wherever a component of the present invention is implemented as software, the component can be implemented as a script, as a standalone program, as part of a larger program, as a plurality of separate scripts and/or programs, as a statically or dynamically linked library, as a kernel loadable module, as a device driver, and/or in every and any other way known now or in the future to those of skill in the art of computer programming. Additionally, the present invention is in no way limited to implementation in any specific programming language, or for any specific operating system or environment. Accordingly, the disclosure of the present invention is intended to be illustrative, but not limiting, of the scope of the invention, which is set forth in the following claims.

In a preferred embodiment, the present invention can be implemented in software. Software programming code that embodies the present invention is typically accessed by a microprocessor or microcontroller from long-term, persistent storage media of some type, such as a flash drive or hard drive. The software programming code may be embodied on any of a variety of known media for use with a data processing system, such as a diskette, hard drive, CD-ROM, or the like. The code may be distributed on such media, or may be distributed from the memory or storage of one computer system over a network of some type to other computer systems for use by such other systems. Alternatively, the programming code may be embodied in the memory of the device and accessed by a microprocessor using an internal bus. The techniques and methods for embodying software programming code in memory, on physical media, and/or distributing software code via networks are well known and will not be further discussed herein.

Generally, program modules include routines, programs, objects, components, data structures and the like that perform particular tasks or implement particular abstract data types. Moreover, those skilled in the art will appreciate that the invention can be practiced with other computer system configurations, including hand-held devices, multi-processor systems, microprocessor-based or programmable consumer electronics, network PCs, minicomputers, mainframe computers, and the like. The invention may also be practiced in distributed computing environments where tasks are performed by remote processing devices that are linked through a communications network. In a distributed computing environment, program modules may be located in both local and remote memory storage devices.

Embodiments of the present invention as have been herein described, may be implemented with reference to various wireless networks and their associated communication devices. For example, the determination of the intermediate brain state goal and binaural tone frequency could be determined remotely. Networks need for such an application can also include mainframe computers or servers, such as a gateway computer or application server (which may access a data repository). A gateway computer serves as a point of entry into each network. The gateway may be coupled to another network by means of a communications link. The gateway may also be directly coupled to one or more devices using a communications link. Further, the gateway may be indirectly coupled to one or more devices. The gateway computer may also be coupled to a storage device such as data repository.

As will be understood by those familiar with the art, the invention may be embodied in other specific forms without departing from the spirit or essential characteristics thereof. Likewise, the particular naming and division of the modules, managers, functions, systems, engines, layers, features, attributes, methodologies, and other aspects are not mandatory or significant, and the mechanisms that implement the invention or its features may have different names, divisions, and/or formats. Furthermore, as will be apparent to one of ordinary skill in the relevant art, that one or more of the modules, managers, functions, systems, engines, layers, features, attributes, methodologies, and other aspects of the invention can be implemented as software, hardware, firmware, or any combination of the three. Of course, wherever a component of the present invention is implemented as software, the component can be implemented as a script, as a standalone program, as part of a larger program, as a plurality of separate scripts and/or programs, as a statically or dynamically linked library, as a kernel loadable module, as a device driver, and/or in every and any other way known now or in the future to those of skill in the art of computer programming. Additionally, the present invention is in no way limited to implementation in any specific programming language, or for any specific operating system or environment. Accordingly, the disclosure of the present invention is intended to be illustrative, but not limiting, of the scope of the invention, which is set forth in the following claims.

While there have been described above the principles of the present invention in conjunction with a system for inducing sleep using binaural tones, it is to be clearly understood that the foregoing description is made only by way of example and not as a limitation to the scope of the invention. Particularly, it is recognized that the teachings of the foregoing disclosure will suggest other modifications to those persons skilled in the relevant art. Such modifications may involve other features that are already known per se and which may be used instead of or in addition to features already described herein. It should be understood that the scope of the disclosure herein also includes any novel features or any novel combination of features disclosed either explicitly or implicitly or any generalization or modification thereof which would be apparent to persons skilled in the relevant art, whether or not such relates to the same invention as presently claimed in any claim and whether or not it mitigates any or all of the same technical problems as confronted by the present invention. The Applicant hereby reserves the right to formulate new claims to such features and/or combinations of such features during the prosecution of the present application or of any further application derived therefrom.

We claim:

1. A system for inducing sleep, comprising
   a dermal sensor operable to detect electrical activity;
   an accelerometer operable to detect changes in motion;
   a binaural tone generator;
   a processor, communicatively coupled to the sensor, the accelerometer, and the binaural tone generator, operable to execute a program of instructions; and
   a non-transitory computer-readable storage medium coupled to the processor and tangibly embodying a set of instructions for inducing sleep, wherein the set of instructions when executed by the processor include the steps for
      determining a current brain state based on a synthesis of detected electrical activity and detected changes in motion wherein detected electrical activity alone or detected changes in motion alone each possess data gaps and are each insufficient in determining the current brain state and wherein the synthesis of detected electrical activity and detected changes in motion bridges the data gaps to determine the current brain state,
      creating a binaural tone from the binaural tone generator based on the current brain state to achieve a target brain state via an intermediate target brain state, wherein the intermediate target brain state is an obtainable transitional state between the current brain state and the target brain state, and wherein the binaural tone induces the detected brain activity to change to the intermediate target brain state while transitioning to the target brain state,
      monitoring the current brain state and,
      responsive to a change in the current brain state, modifying creation of the binaural tone and the intermediate target brain state to induce the current brain state to change, and
      upon reaching the target brain state, ceasing creation of the binaural tone.

2. The system for inducing sleep according to claim 1, wherein the binaural tone generator is operable to produce a first tone of a first frequency associated with a first earphone and a second tone of a second frequency associated with a second ear phone, the first frequency differing from the second frequency, and wherein responsive to the first tone and the second tone being concurrently sensed by a first ear and a second ear of an individual, respectively, the first tone and the second tone are interpreted by the individual as a resonate beat.

3. The system for inducing sleep according to claim 2, wherein the resonant beat is based on the intermediate target brain state.

4. The system for inducing sleep according to claim 1, wherein the target brain state is a stage 3 sleep state.

5. The system for inducing sleep according to claim 1, wherein the target brain state is delta brain waves.

6. The system for inducing sleep according to claim 1, wherein the sensor is an electroencephalograph.

7. The system for inducing sleep according to claim 1, wherein the sensor is a magnetoencephalograph.

8. The system for inducing sleep according to claim 1, wherein the sensor is an electrocorticograph.

9. The system for inducing sleep according to claim 1, wherein the sensor measures ionic current flows within brain neurons.

10. The system for inducing sleep according to claim 1, wherein a change in motion is indicative of a state of sleep.

11. The system for inducing sleep according to claim 1, wherein the sensor is an actimetry sensor.

12. A method for inducing a sleep state using binaural tones, the method comprising:
   positioning, by a band, a dermal sensor so as to establish continual surface contact with skin on the forehead of a user, wherein the dermal sensor detects electrical activity of the user;
   collecting brain state data wherein brain state data includes a synthesis of detected electrical activity and changes in motion detected by an accelerometer;
   analyzing collected brain state data to determine a current activity state wherein detected electrical activity alone or changes in motion detected by the accelerometer alone each possess data gaps and are each insufficient to determine the current brain state and wherein the synthesis of detected electrical activity and changes in motion detected by the accelerometer bridges the data gaps to determine the current activity state;
   comparing the current activity state to a goal state;
   responsive to the current activity state differing from the goal state, determining a suggestive binaural tone frequency and an intermediate goal state, wherein the intermediate goal state is interposed between the current activity state and the goal state;

applying the suggestive binaural tone to adjust the current activity state to the intermediate goal state;

monitoring the current activity state to determine whether the suggestive binaural tone influences the current activity state to change toward the intermediate goal state; and responsive to the suggestive binaural tone changing the current activity state toward the intermediate goal state, iteratively adjusting the intermediate goal state toward the goal state and the suggestive binaural tone to transition the current activity state to the goal state, and responsive to achieving the goal state, ceasing application of the suggestive binaural tone.

13. The method for inducing a sleep state using binaural tones according to claim 12, wherein collecting brain state data includes collecting brain wave data.

14. The method for inducing a sleep state using binaural tones according to claim 12, wherein collecting brain state data includes collecting ionic current flows within brain neurons to determine brain wave data.

15. The method for inducing a sleep state using binaural tones according to claim 12, wherein collecting brain state data includes measuring ionic current flows within brain neurons using an electroencephalograph.

16. The method for inducing a sleep state using binaural tones according to claim 12, wherein collecting brain state data includes measuring a change in motion.

17. The method for inducing a sleep state using binaural tones according to claim 12, wherein collecting brain state data includes measuring motion of the user during sleep.

18. The method for inducing a sleep state using binaural tones according to claim 12, wherein the suggestive binaural tone frequency is set in a range of 1-3 Hz below the current activity state.

19. The method for inducing a sleep state using binaural tones according to claim 12, responsive to the current activity state being identical to the goal state, terminating binaural tone generation.

20. The method for inducing a sleep state using binaural tones according to claim 12, wherein the goal state is a stage 3 sleep state.

21. The method for inducing a sleep state using binaural tones according to claim 12, wherein the goal state is delta brain waves.

22. A method for inducing sleep using binaural tones comprising:
positioning a dermal sensor on the forehead of a user to detect a plurality of electrical signals generated by the user and an accelerometer proximate to the dermal sensor to detect changes in motion of the user;
identifying a first brain activity state data wherein the first brain activity state data includes a synthesis of detected electrical activity and detected changes in motion and wherein detected electrical activity alone or detected changes in motion alone each possess data gaps and are each insufficient in identifying a first brain activity state and wherein the synthesis of detected electrical activity and detected changes in motion bridges the data gaps to determine the first brain activity state; and
driving the first brain activity state to a second brain activity state using a decreasing frequency progression of binaural tones wherein an initial binaural tone frequency is interposed between the first brain activity state and the second brain activity state and wherein the decreasing frequency progression is based on an iterative determination of current brain activity based on detected activity data.

23. The method for inducing sleep using binaural tones of claim 22, wherein the dermal sensor is a single dermal sensor.

24. The method for inducing sleep using binaural tones of claim 23, wherein the single dermal sensor includes an electroencephalograph.

25. The method for inducing sleep using binaural tones of claim 23, wherein the single dermal sensor includes an actigraphy sensors.

26. The method for inducing sleep using binaural tones of claim 22 wherein responsive to driving the first brain activity state to the second brain activity state, ceasing use of binaural tones.

27. The method for inducing sleep using binaural tones of claim 22, wherein the decreasing frequency progression of binaural tones is based on a predetermined schedule.

28. The method for inducing sleep using binaural tones of claim 22, wherein the decreasing frequency progression of binaural tones is based on an iterative determination of a current brain state.

29. A system for inducing sleep, comprising:
an adaptable band wherein the adaptable band circumscribes the head of a user;
one or more sensors affixed to the adaptable band and operable to collect data indicative of brain activity;
a binaural tone generator affixed to the adaptable band;
a microcontroller communicatively coupled to the one or more sensors and the binaural tone generator, and operable to execute a program of instructions; and
a non-transitory computer-readable medium coupled to the microcontroller and tangibly embodying a set of instructions for inducing sleep wherein one portion of the set of instructions is configured to iteratively determine a current brain state based on a synthesis of collected brain activity data and detected changes in motion, wherein collected brain activity data alone or detected changes in motion alone each possess data gaps and are insufficient to determine the current brain state and wherein the synthesis of collected brain activity data and detected changes in motion bridges the data gaps to determine the current brain state, and direct the binaural tone generator to generate a decreasing frequency progression of binaural tones based on iteratively monitoring the current brain state and a target brain state.

30. The system for inducing sleep of claim 29 wherein one of the one or more sensors is a dermal sensor that detects electrical activity of the user.

31. The system for inducing sleep of claim 29 wherein one of the one or more sensors is an accelerometer that detects changes in motion of the user.

32. The system for inducing sleep of claim 29 wherein one of the set of instructions is configured to iteratively determine the current brain state and modify the decreasing frequency progression of binaural tones accordingly.

* * * * *